United States Patent
Freeman et al.

(10) Patent No.: US 10,390,727 B2
(45) Date of Patent: Aug. 27, 2019

(54) APPARATUS AND METHOD FOR IMAGING CURRENTS USING NANOPARTICLES AND LOW-FIELD MAGNETIC RESONANCE IMAGING (MRI)

(71) Applicants: The Charles Stark Draper Laboratory, Inc., Cambridge, MA (US); The General Hospital Corporation, Boston, MA (US)

(72) Inventors: Daniel K. Freeman, Reading, MA (US); Matthew Rosen, Boston, MA (US)

(73) Assignees: THE CHARLES STARK DRAPER LABORATORY, INC., Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 186 days.

(21) Appl. No.: 15/493,715

(22) Filed: Apr. 21, 2017

(65) Prior Publication Data
US 2018/0303373 A1    Oct. 25, 2018

(51) Int. Cl.
| A61B 5/055 | (2006.01) |
| G01R 33/56 | (2006.01) |
| G01R 33/48 | (2006.01) |
| G01R 33/44 | (2006.01) |
| A61B 5/00 | (2006.01) |
| A61B 5/05 | (2006.01) |
| G01R 33/561 | (2006.01) |

(52) U.S. Cl.
CPC ............ *A61B 5/055* (2013.01); *A61B 5/0042* (2013.01); *A61B 5/0515* (2013.01); *G01R 33/445* (2013.01); *G01R 33/4806* (2013.01); *G01R 33/5601* (2013.01); *G01R 33/5614* (2013.01)

(58) Field of Classification Search
CPC ..... A61B 5/055; A61B 5/0042; A61B 5/0515; G01R 33/5601; G01R 33/4806; G01R 33/445
See application file for complete search history.

(56) References Cited

U.S. PATENT DOCUMENTS

| 5,303,705 A | 4/1994 | Nenov |
| 5,842,986 A * | 12/1998 | Avrin ................. A61B 5/04005 600/407 |

(Continued)

FOREIGN PATENT DOCUMENTS

WO    2008152109    12/2008

OTHER PUBLICATIONS

Rakesh Guduru; "Bionano Electronics: Magneto-Electric Nanoparticles for Drug Delivery, Brain Stimulation and Imaging Applications;" Florida International University; 2013.

*Primary Examiner* — Dixomara Vargas
(74) *Attorney, Agent, or Firm* — Burns & Levinson, LLP; Joseph M. Maraia

(57) ABSTRACT

A system and method for imaging in connection with electrical currents includes nanoparticles introduced into a region in which the electrical currents are present. A low-field magnetic resonance imaging (MRI) scanner detects an effect of a magnetic field generated by interaction of the nanoparticles with the electrical currents in the region. The MRI scanner operates at a magnetic field intensity below a level at which the nanoparticles would be magnetically saturated.

20 Claims, 4 Drawing Sheets

(56) References Cited

U.S. PATENT DOCUMENTS

| | | | |
|---|---|---|---|
| 6,278,893 B1* | 8/2001 | Ardenkj.ae butted.r-Larson | A61K 49/08 324/307 |
| 6,466,814 B1* | 10/2002 | Ardenkjaer-Larsen | A61K 49/08 324/307 |
| 9,395,425 B2* | 7/2016 | Diamond | A61B 5/04008 |
| 10,194,829 B2* | 2/2019 | Kaditz | A61B 5/055 |
| 2009/0004113 A1* | 1/2009 | Wolf | A61B 5/0515 424/9.2 |
| 2011/0306870 A1* | 12/2011 | Kuhn | A61B 5/0515 600/411 |
| 2012/0105061 A1* | 5/2012 | Drake | G01R 33/10 324/318 |
| 2012/0179029 A1* | 7/2012 | Kircher | A61B 5/0042 600/421 |
| 2019/0033415 A1* | 1/2019 | Sofka | A61B 5/0042 |

\* cited by examiner

APPARATUS AND METHOD FOR IMAGING CURRENTS USING NANOPARTICLES AND LOW-FIELD MAGNETIC RESONANCE IMAGING (MRI)

BACKGROUND

1. Technical Field

The present disclosure is related magnetic resonance imaging (MRI) and, in particular, to an apparatus and method for imaging currents such as neuronal currents using nanoparticles and low-field MRI.

2. Discussion of Related Art

A variety of techniques have been developed to noninvasively image human brain function to develop a better understanding how the brain works and to detect brain pathology, for example, autism, epilepsy, schizophrenia, Alzheimer's, etc. There are currently no available methods to sense directly the electrical activity in the brain, i.e., neuronal currents, using MRI. Such a capability would enable investigations into the underlying neural abnormalities in patients with autism, schizophrenia, Alzheimer's, etc.

SUMMARY

According to one aspect, a method of imaging in connection with electrical currents is provided. According to the method, nanoparticles are introduced into a region in which the electrical currents are present. An effect of a magnetic field generated by interaction of the nanoparticles with the electrical currents in the region is detected using a low-field magnetic resonance imaging (MRI) scanner. The MRI scanner operates at a magnetic field intensity below a level at which the nanoparticles would be magnetically saturated.

In some exemplary embodiments, the electrical currents are neuronal currents. The region can comprise at least a portion of a human brain.

In some exemplary embodiments, the magnetic field intensity is below 0.1 Tesla.

The nanoparticles can comprise a ferromagnetic material. The nanoparticles can comprise a ferroelectric material. In some exemplary embodiments, the nanoparticles can comprise both a ferromagnetic material and a ferroelectric material. For example, the nanoparticles comprise cobalt ferrite and/or barium titanate.

According to another aspect, a system for imaging in connection with electrical currents is provided. In the system nanoparticles are introduced into a region in which the electrical currents are present. A low-field magnetic resonance imaging (MRI) scanner detects an effect of a magnetic field generated by interaction of the nanoparticles with the electrical currents in the region. The MRI scanner operates at a magnetic field intensity below a level at which the nanoparticles would be magnetically saturated.

In some exemplary embodiments, the electrical currents are neuronal currents. The region can comprise at least a portion of a human brain.

In some exemplary embodiments, the magnetic field intensity is below 0.1 Tesla.

The nanoparticles can comprise a ferromagnetic material. The nanoparticles can comprise a ferroelectric material. In some exemplary embodiments, the nanoparticles can comprise both a ferromagnetic material and a ferroelectric material. For example, the nanoparticles comprise cobalt ferrite and/or barium titanate.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings.

DETAILED DESCRIPTION

Figure 1:
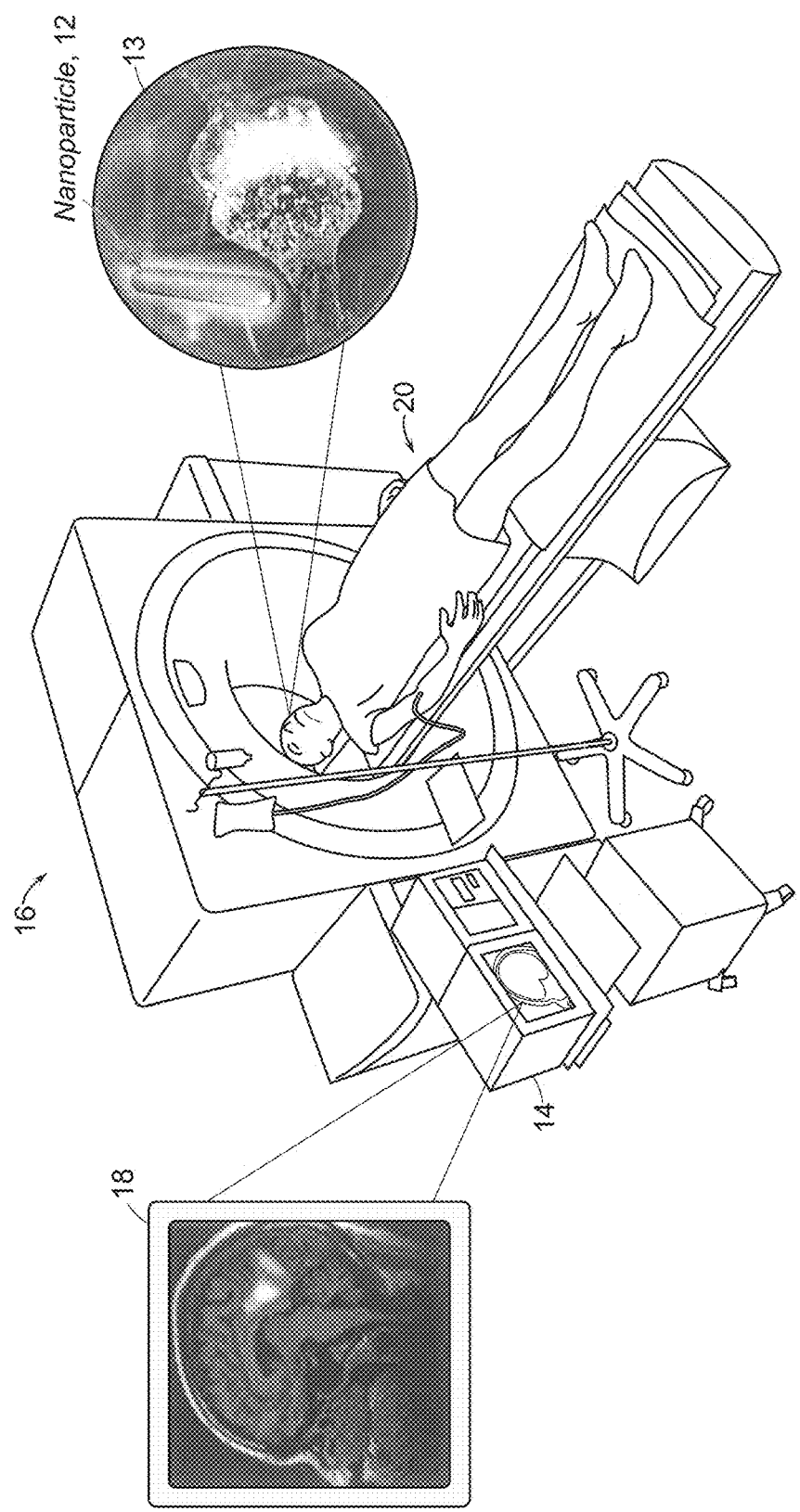
FIG. 1 includes a schematic diagram of a system for imaging neuronal currents in a human brain using nanoparticles and low-field magnetic resonance imaging (MRI), according to some exemplary embodiments.

The present disclosure is directed to the use of a certain class of nanoparticles with low-field MRI to image neuronal currents. The nanoparticles exhibit magneto-electric properties. One example is a material that contains cobalt ferrite, a ferromagnetic material, and barium titanate, a ferroelectric material. Such nanoparticles will generate a magnetic field when exposed to an electric field and will generate an electric field when exposed to a magnetic field.

According to the present disclosure, when placed in the brain, these nanoparticles will be exposed to electric fields generated by neurons and will generate a magnetic field that will influence the spin of water protons. This spin of the water protons can then be detected by an MRI scanner. Because these nanoparticles contain ferromagnetic material, they are susceptible to saturation in the high magnetic field environment of a typical MRI scanner, having a magnetic field intensity of, for example, approximately 1.5 Tesla. Therefore, according to the present disclosure, these nanoparticles are used in a low-field MRI, with magnetic field intensity levels that are below the saturation of the nanoparticles. For example, in a low-field MRI scanner used according to the present disclosure field intensity can nominally be approximately 0.005 Tesla. In general, according to the present disclosure, the field intensity of the low-field MRI is no greater than 0.1 Tesla.

According to some exemplary embodiments, magneto-electric nanoparticles (MENs) can be intravenously administered and forced across the blood-brain barrier such as via the sinus or via spinal tap/spinal fluid. The MENs can be, for example, $CoFe_2O_4$-$BaTiO_3$ 30-nm nanoparticles.

A neural network can be considered as a complex bioelectric circuit made of many neurons connected through chemical and electrical synapses formed between axons and dendrites. The signaling in the network is electric-field driven and based on a highly collective system of electric charges, neurotransmitters and action potentials. The ability to remotely incite specific neuronal excitations deep in the brain with the purpose to artificially stimulate selective regions of the network remains an important open question in neural engineering. Furthermore, the ability to control the central nervous system (CNS) at the micro- or nano-scale could provide unprecedented control of specific functions and enable highly personalized pin-point treatment of neurodegenerative diseases such as Parkinson's disease, Essential Tremor, Epilepsy, and others.

Current brain stimulation technology is operated at macroscale and often relies on highly-invasive direct-contact-electrode techniques such as deep-brain stimulation (DBS); it can be noted that DBS is one of only a few neurosurgical methods allowed for blinded studies. There are also noninvasive brain stimulation methods; these include repetitive transcranial magnetic stimulation (rTMS) and transcranial direct current stimulation. Though rTMS and transcranial direct current stimulation represent major technological advances in noninvasive brain stimulation, the depth and locality of focusing are strongly limited in both methods. In rTMS, relatively high intensity magnetic fields (on the order of 10,000 Oe) are required to stimulate regions deep in the brain; however, high intensity magnetic fields, especially in the a.c. mode, may lead to excessive energy dissipation or other destructive side effects. The required high external magnetic field can be explained by the relatively weak coupling between the magnetic field and the local electric currents in the neural system.

Thus, one can identify the following engineering bottleneck. On one hand, using electric fields, one can achieve adequate brain stimulation; however, the need to establish direct contact with individual neurons makes the electric field stimulation highly invasive. It is hard to see how such a physical direct contact with each of the 75 billion neurons in the brain can be achieved. On the other hand, magnetic fields can penetrate through the brain without being significantly distorted by the local microenvironment and therefore can be used for externally controlled stimulation; however, inadequately weak coupling between external magnetic fields and intrinsic neural activity-induced electric currents makes such stimulation relatively inefficient and consequently inadequate for being used for local stimulation deep in the brain.

One potential solution for enabling high-efficacy remote control of the neural activity deep in the brain would be to use conventional magnetic nanoparticles (MNs) to locally amplify the magnetic field and thus enhance the effective coupling to local electric currents. An even more dramatic solution could be achieved by using a class of functional nanoparticles known as magnetoelectric nanoparticles (MENs). Under an equivalent magnetic field exposure, MENs not only can amplify the local magnetic field but also generate an additional local electric field. The field is generated due to the nonzero magnetoelectric (ME) effect, which originates from an intrinsic coupling between electric and magnetic fields in MENs. As a result, when administrated in the brain, MENs can serve as nanoscale sits which, when exposed to a relatively low external magnetic field (in the range of 100-1000 Oe), generate local electric fields (on the order of 1000 V/m or higher) to provide direct external access to the internal (bioelectric) neural circuits. In other words, MENs enable a unique way to combine the advantages of both the high efficacy of the electric fields and the external-control capability of the magnetic fields and therefore open a pathway to control the brain.

Thus, toxicity-free MENs can be used to stimulate the brain via application of low external magnetic fields. Furthermore, in accordance with the present disclosure, as described above, these MENs will be exposed to electric fields generated by neurons and will generate a magnetic field that will influence the spin of water protons. This spin of the water protons can then be detected by a low-field MM scanner, of the type described below in detail.

Magnetic Resonance Imaging (MRI) is superior in its ability to visualize anatomical structure and function non-invasively with high spatial and temporal resolution. Yet to overcome the low sensitivity inherent in inductive detection of weakly polarized nuclear spins, the vast majority of clinical MRI scanners employ superconducting magnets producing very high magnetic fields. Commonly found at 1.5-3 tesla (T), these powerful magnets are massive and have very strict infrastructure demands that preclude operation in many environments. MRI scanners are costly to purchase, site, and maintain, with the purchase price approaching $1 M per tesla (T) of magnetic field. The present disclosure includes a, non-cryogenic approach to high-performance human MRI at ultra-low magnetic field, whereby modern under-sampling strategies are combined with fully-refocused dynamic spin control using steady-state free precession techniques. At 6.5 mT (more than 450 times lower than clinical MRI scanners) described is (2.5×3.5× 8.5) mm imaging resolution in the living human brain using a simple, open-geometry electromagnet, with 3D image acquisition over the entire brain in 6 minutes. These practical ultra-low magnetic field implementations of MRI (<10 mT) will complement traditional MRI, providing clinically relevant images and setting new standards for affordable (<$50,000) and robust portable devices.

Magnetic Resonance Imaging (MRI) is a powerful, non-invasive technique for revealing the internal structure and function of the human body with a rich range of biological contrasts. Despite considerable improvements in imaging quality and speed, the underlying technology remains remarkably unchanged compared to the first generation scanners that emerged on the market 30 years ago. The fact that very strong magnetic fields are needed to overcome the intrinsic lack of sensitivity of NMR-based methods continues to dominate scanner construction, and drives both pricing and scanner siting requirements. MRI scanners are built around massive superconducting magnets with a nominal cost of $1 M per tesla of magnetic field. With 1.5 tesla (T) and 3 T scanners in common use, and increasing demand for 7 T, the extreme cost of these devices limits the number of scanners on site and requires hospitals to carefully prioritize patients. Additionally, these massive scanners are strictly confined to the MRI suite within a hospital thus precluding mobile operation in many environments including surgical intervention, triage and primary care suites.

One of the next revolutions in health care will center on cost-effectiveness. Thus, the prospect of low-cost (<$50.000) but high-performance MRI systems to complement traditional MRI scanners is compelling. A promising solution is MRI at very low magnetic field where scalable electro-magnets become practical. Operation at low magnetic field enables imaging in environments where high magnetic fields would be contraindicated (such as in the presence of nearby ferrous materials), and raises the potential for scanners to be built at significantly reduced total cost, and with open geometry designs that ease patient handling and positioning.

The unique role that very low magnetic field MRI scanners can play in neurocritical care was recognized 30 years ago in the pioneering work of Sepponnen, et al., who explored the clinical validity of brain MRI acquired in a 20 mT scanner located in a hospital emergency department. These early images were acquired at the lowest field strength reported in clinical MRI at that time, and although limited to a single 15 mm slice, were obtained with good contract in a reasonable four minute acquisition.

In an effort to improve the performance of very low field MRI systems, Macovski and Conolly introduced the concept of pre-polarized MRI (also known as PMRI) in 1993, which employs a strong, inhomogeneous pulsed magnet field to generate increased nuclear polarization, and a second much weaker homogeneous magnetic field for signal detection. This PMRI strategy has been the acquisition strategy for nearly all very low field MRI systems since its introduction. In 2006, PMRI in human subjects with metal implants was reported in vivo in human wrists, where a 0.4 T field was used for pre-polarization, and a 54 mT field used for signal detection.

The ultra-low field (ULF) MRI regime is defined when the magnetic field used for signal detection is below 10 mT. In 2007, PMR1 was demonstrated with detection in the ULF regime, orders of magnitude lower than reported in Venook et al., using arrays of very sensitive superconducting quantum interference devices (SQUIDs) as magnetometers to measure the spatially encoded nuclear spin precession. Pre-polarized cryogenic SQUID-detected ULF MRI has been demonstrated in the human brain as well as in the human hand and wrist by several groups. Results from late 2013 demonstrate in vivo 2D images of the human brain (pre-polarized to 80 mT) with (2.5×1.9) mm in-plane resolution over a (10×10) cm$^2$ region of interest and a 100 mm thick slice, acquired in ~26 minutes. Very recent results from the Los Alamos ULF effort demonstrate 3D images of the human brain (pre-polarized to 100 mT) with (2.1×2.4×15) mm$^3$ resolution (5 slices) in 67 minutes.

Although SQUIDs are the most technically mature of the non-inductive magnetometers used at ULF, several alternative detection technologies have been explored. Optical measurement of nitrogen-vacancy (NV) color centers in diamond form the basis of robust solid-stale magnetometers with unmatched magnetic field sensitivity at nanoscale resolutions. As of yet, however, NV-diamond magnetometers do not provide obvious benefits for human scale MRI. Atomic magnetometers (AM) have also been applied to pre-polarized NMR and MRI, and improvements in these devices have resulted in a magnetic field sensitivity approaching SQUID performance without the need for cryogenics. The first attempt at imaging the living human brain with an atomic magnetometer was reported in 2013. In this work, nuclear spins are pre-polarized at 80 mT and detection is performed at 4 mT. Despite the ultra-high sensitivity and dynamic range of the AM magnetometer, the setup as described provides limited 3D coverage and significant improvement in resolution and SNR (Signal-to-Noise Ratio) is needed in order to clearly discern anatomical features, which will inevitably increase the acquisition time.

Independent of which detection technology is used, all pre-polarized ULF MRI suffers from intrinsically long acquisition times, most of which is incompressible, that result from the time needed to generate nuclear polarization. In the present work, we demonstrate fast and efficient brain ULF MRI at 6.5 mT with no pre-polarization nor cryogenics, combining under-sampling strategies with a high performance fully refocused steady-state-based acquisition in a simple, inexpensive system. With a novel inductive single channel detector, we report the fastest 3D MRI of the living human brain in the ULF regime compared to the state-of-the-art as reported in the literature.

Ultra-Low Field Acquisition Strategy.

High performance imaging at ultra-low magnetic field focuses on significantly reducing acquisition time using fast imaging techniques. Here, fast imaging was enabled using 3D balanced steady state free precession sequences (b-SSFP). Originally described by Carr in 1958 as a technique for improving the signal-to-noise ratio (SNR) in NMR experiments, b-SSFP was implemented as an efficient acquisition strategy for MRI In 1986 by Oppelt et al., and extensively investigated in the early 2000 s. Unlike traditional gradient- and spin-echo techniques, b-SSFP sequences dynamically refocus spin magnetization following measurement, eliminating the extra delays typically used for $T_2$ decay and $T_1$ recovery. This considerably reduces acquisition times and provides the highest SNR per unit time of all imaging sequences. These sequences are very sensitive to the amount of spin dephasing that occurs between consecutive RF pulses (the pulse repetition time, TR), and typical banding artifacts are expected to appear within a range of +1/(2*TR) Hz that result from inhomogeneity in the state magnetic field. This sets a strict requirement on the absolute field homogeneity over the field-of-view (FOV), which for operation at 3 T is typically at the sub-PPM level.

In the millitesla regime, however, the fractional homogeneity requirement is three orders of magnitude lower, significantly easing the engineering burden for low-field magnet design. With a current TR=22.5 ms, our b-SSFP sequence is completely immune to banding artifacts for up to 160 ppm inhomogeneity at 6.5 mT. Furthermore, magnetic susceptibility differences are significantly reduced at ULF, preventing off-resonance b-SSFP artifacts. As a result, provided reasonable magnetic field homogeneity, b-SSFP at very low magnetic field alleviates the necessity of ultra-short TRs and provides good image quality over a large FOV without the need for sophisticated ultrafast gradient power amplifiers. Our 6.5 mT MRI scanner was upgraded for improved $B_0$ stability, and was used for all the low-field b-SSFP experiments described here.

RF Coil Design.

The design of inductive detection coils for use in ULF MRI presents a different set of challenges to those present in conventional high-field MRI. In particular, issues of coil resistance and probe bandwidth manifest differently. In conventional MRI, the dominant source of noise is the presence of small currents in the lossy sample (the so-called "body noise" regime) to which a characteristic sample resistance Rs is attributed. Both the sample and the coil contribute to Johnson noise but in practice Rs is much larger than the coil resistance Re (i.e. Rs>>Rc), and thus Re can be neglected in SNR calculations. However, at low field, Rs becomes much smaller and Re becomes the dominant noise contribution (i.e., the so-called Johnson noise dominated regime). To minimize the coil resistance in a simple design, larger diameter wire or stranded litz wire can be used, but one needs to consider the impact this has on coil bandwidth. Given the maximum imaging gradient strength of ~1 mT/m attainable in our 6.5 mT electro-magnet Low Field Imager (LFI), a 20 cm (head-sized) FOV will span a frequency encode bandwidth of ~10 kHz. This sets the minimum bandwidth needed for the detection circuit so as to not significantly convolve the coil response function with the object being imaged. At our Larmor frequency of 276 kHz, this corresponds to a maximum coil Q of ~30. A single channel inductive coil for operation at 276 kHz (FIG. 2) was designed and built using 3D printing fused deposition modeling technology and multi-strand litz wire. A 30-turn 3D Archimedean spiral with an aligned turn-to-turn distance of 5.6 mm guided wire placement, thus ensuring that $B_1$ produced by the spiral pattern is everywhere orthogonal to the main magnetic field $B_0$. The hemispherical spiral design results in a very homogeneous magnetic field over the volume of interest, making it suitable for both RF transmit and receive. The number of turns in the coil was chosen to obtain the inductance needed to achieve the desired Q. Litz wire was preferred in this low frequency application due to its lower AC resistance compared to solid copper wire of the same physical size.

Image Reconstruction and Processing.

MrI images are reconstructed from frequency- and phase-encoded information in the k-space formalism. Previously, we described our use of under-sampling strategies to accelerate low-field imaging. We make use of this here by randomly sampling 50% of k-space using a variable density Gaussian pattern. The variable density Gaussian sampling pattern emphasizes sampling in the center of k-space, where most of the information is located, and randomly skips lines near the edges. The resulting images do not exhibit coherent artifacts, such as typical wrap-around ghosts due to POV contraction. Missing values in the acquired k-space were set to zero. The standard deviation of the sampling pattern as a fraction of the POV was optimized to preserve adequate high-frequency information. Once reconstructed, the images were apodized and processed using Perona and Malik anisotropic diffusion filtering (ADF). ADF is a powerful denoising filter that convolves images of interest with adaptive Gaussian kernels. The Perona and Malik approach works as an iterative multi-scale smoothing and edge detection process that removes noise but prevents image blurring by adjusting filter sharpness as a function of signal intensity gradients.

In Vivo Brain MRI at 6.5 m T.

Three-dimensional under-sampled images were acquired at 6.5 mT in 6 minutes for each of the three spatial orientations (axial, coronal, and sagittal). The maximum image SNR was computed from the ratio of maximum signal amplitude to the standard deviation over a user defined noise region; SNR of 15, 21, and 16 were measured in axial, coronal, and sagittal orientations respectively. With a maximum gradient strength of ~1 mT·m$^{-1}$ and maximal slew rate of 0.7 mT m$^{-1}$ ms$^{-1}$, no artifacts from concomitant field effect are seen over the 20 cm field of view. The sinuses are easily recognizable in black on the images, as well as the skull. Surrounding the brain, we can identify the dura in bright grey on coronal and sagittal images. In the brain, the two hemispheres and the cerebellum are distinct, and cortical tissue can be distinguished from white matter. Liquid compartments, here CSF, appear in bright grey and white. Images acquired in the axial orientation are compared to images acquired in the same subject at high magnetic field (3 T) using traditional $T_1$, $T_2$, proton density (PD) weighted sequences. In b-SSFP, contrast is related to the $T_1/T_2$ ratio of the images sample. At high field, liquids and tissue typically have rather different relaxation times but at 6.5 mT their ration ($T_1/T_2$) is of order unity resulting in the distinct PD-weighted contrast. Most of the anatomic features seen at 3 T can be identified in the ultra-low-field scans.

The maximum SNR in the high field (HF) b-SSFP image is 317. In order to interpret the difference in SNR between the HF and the ULF scans, we scale the HF image SNR by a factor corresponding to the difference in the ULF spatial resolution (2.5×3.5×8.5 in the axial orientation), and by a second factor to account for signal averaging as done at ULF (Fig. Sb, NA=160). The SNR in the downscaled HF scan is equivalent to 317×(2.5×3.5×8.5)×/160=300000, which gives the ratio $SNR_{ST}/SNR_{0.0065}$=8300 in the axial orientation. If we assume similar coil performance, and neglect the difference in magnetization at steady state for the two magnetic fields, the resulting 8300-fold difference in SNR agrees reasonably well with the simplified approximation that SNR increases with magnetic field to the 3/2 power, here $460^{3/2}$=9866. Strong banding artifacts appear at high field, mainly due to magnetic susceptibility differences at the air-tissue interface. At 276 kHz, on the otherhand, no imaging artifact is seen over a 20 cm POV despite a 3× longer TR. Our results demonstrate excellent immunity to magnetic field inhomogeneity of the order of ±22 Hz, i.e., 160 ppm at 6.5 mT.

The present disclosure demonstrates the shortest acquisition times and highest SNR per unit time in ULF MRI to date owing to our use of modern sparse sampling strategies and a fully refocused sequence in an optimized electromagnet scanner. These images were acquired without pre-polarization techniques, at a fixed magnetic field and with a simple single channel inductive detector. With an eye towards optimization, we note that for a given spatial resolution, the minimum TR- and consequently the total scan time-is limited by the maximum attainable time-integrated gradient strength. The maximum gradient strength in the LFI is currently −1 mT·m$^{-1}$ resulting in a minimum TR of −23 ms. Weak gradients especially impact phase encoding in balanced sequences like b-SSFP, as every phase-encode pulse is paired with an opposite polarity rewinding pulse. An increase in gradient strength would allow shorter phase encode pulses, thus decreasing total imaging time while maintaining SNR, provided that image distortion from non-linear magnetic fields that accompany the desired encoding gradient (the so called "concomitant field" artifacts) can be mitigated. At 6.5 mT, an increase in gradient strength in the range of 2-5×, combined with efficient strategies to eliminate concomitant field artifacts, can reasonably be envisioned. Additionally, improvements in the electronic noise floor can go a long way to improving scanner sensitivity. In our system, the scanner noise floor is dominated by poor filtering of the high cur-rent lines from the gradient power amplifiers into the RF shielded enclosure of the LFI. More effective filtering of electronic noise coming from our gradient power amplifiers would reduce our system noise floor by a measured factor of 3, thus decreasing the total acquisition time by another factor of $3^2$=9. As SNR increases with magnetic field to the 3/2 power, a simple doubling of magnetic field would result in a sequence about 8 times faster with similar SNR. In the case of human brain imaging, images with similar resolution and SNR as presented here could be then acquired in less than 3 seconds in such an optimized scanner.

A key challenge in obtaining clinically relevant MRI images at ULF is the ability to acquire $T_1$ and/or $T_2$ relaxation-weighted images, and thereby provide contrast to different types of tissue. Typically, magnetization prepared gradient-echo, and spin-echo sequences are used to obtain relaxation-weighted images, but these types of imaging experiments become prohibitively time consuming at ultra-low magnetic fields where signal averaging and recovery of the longitudinal magnetization are required. We have investigated a new strategy to provide contrast based on b-SSFP called "magnetic resonance fingerprinting" (MRF), and have successfully started its implementation at 6.5 mT.

Finally, theoretical frameworks exist that allow image reconstruction of highly undersampled datasets with multiple channel acquisition schemes combining high under-sampling rates with parallel imaging techniques such as SENSE or GRAPPA[58] could reduce the total acquisition time even further, to less than a second. Recent work from Murphy et al. successfully mitigates the computational expense by exploiting massively parallelized computing.

We contend that ULF MRI scanners operating at this expected level of performance could complement traditional MRI by relieving hospital congestion and shortening triage delays. Outside of the radiology suite, mobile ULF scanners might be deployable during military conflicts or during sport events and enable the acquisition of immediate after-trauma knowledge, typically in the case of traumatic brain injuries. Finally, ULF MRI technology may allow resource-poor environments access to MRI systems, without the strict siting requirements and high costs of conventional scanners.

FIG. 1 includes a schematic diagram of a system for imaging neuronal currents in a human brain using nanoparticles and low-field magnetic resonance imaging (MRI), according to some exemplary embodiments. Referring to FIG. 1, a plurality of nanoparticles 12, such as the nanoparticles described above in detail, are introduced into the brain 13 of a human subject 20, such as by intravenous injection. The nanoparticles can be forced across the blood-brain barrier such as via the sinus or via spinal tap/spinal fluid. A low-field MRI system 16, such as the low-field MRI systems described herein in detail, is used to generate an image 18 from brain 13 of human subject 20 on system display 14.

Figure 2:
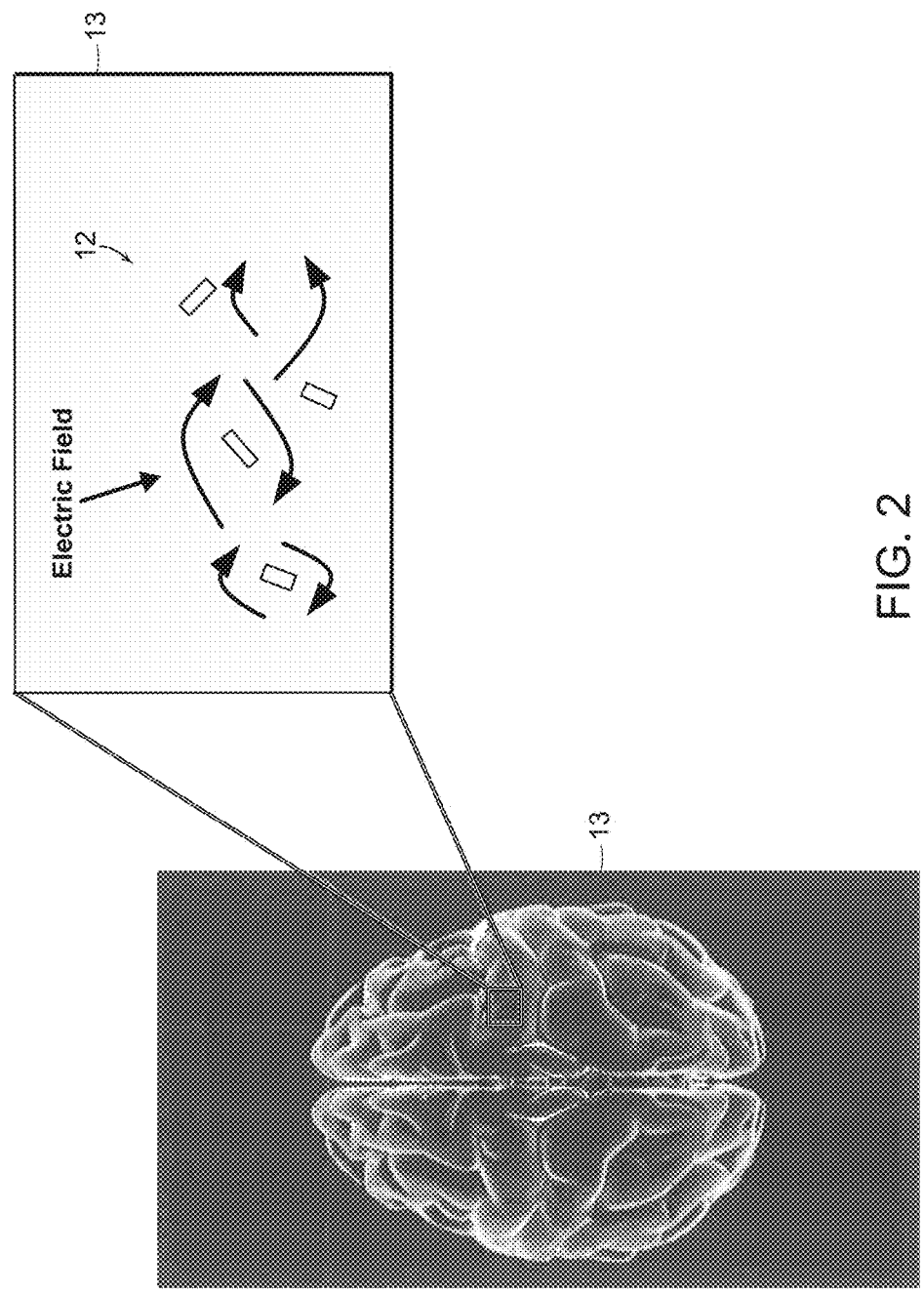
FIG. 2 includes schematic diagrams illustrating nanoparticles interacting with electric fields due to neuronal currents in a human brain for imaging using low-field magnetic resonance imaging (MRI), according to some exemplary embodiments.

FIG. 2 includes schematic diagrams illustrating nanoparticles interacting with electric fields due to neuronal currents in a human brain for imaging using low-field magnetic resonance imaging (MRI), according to some exemplary embodiments. Referring to FIG. 2, neuronal currents in brain 13 induce electric fields, which interact with nanoparticles 12 placed in brain 13 to generate magnetic fields.

Figure 3A:
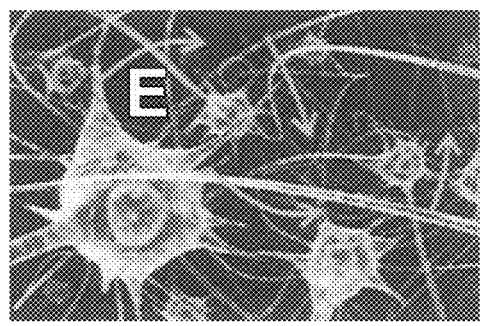
FIGS. 3A through 3D include schematic diagrams illustrating an approach to imaging neuronal currents in a human brain using nanoparticles and low-field magnetic resonance imaging (MRI), according to some exemplary embodiments.
Figure 3B:
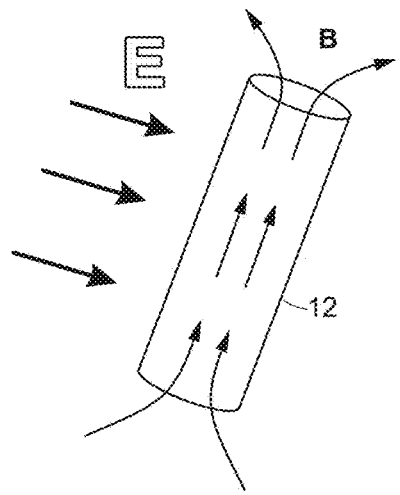
Figure 3C:
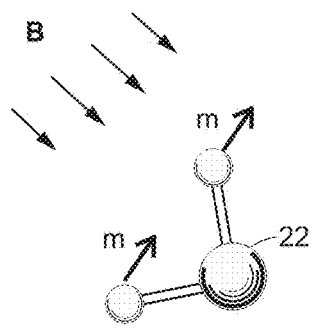
Figure 3D:
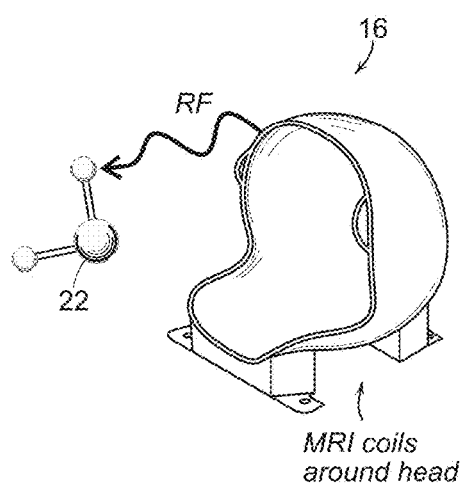
Figure 4:
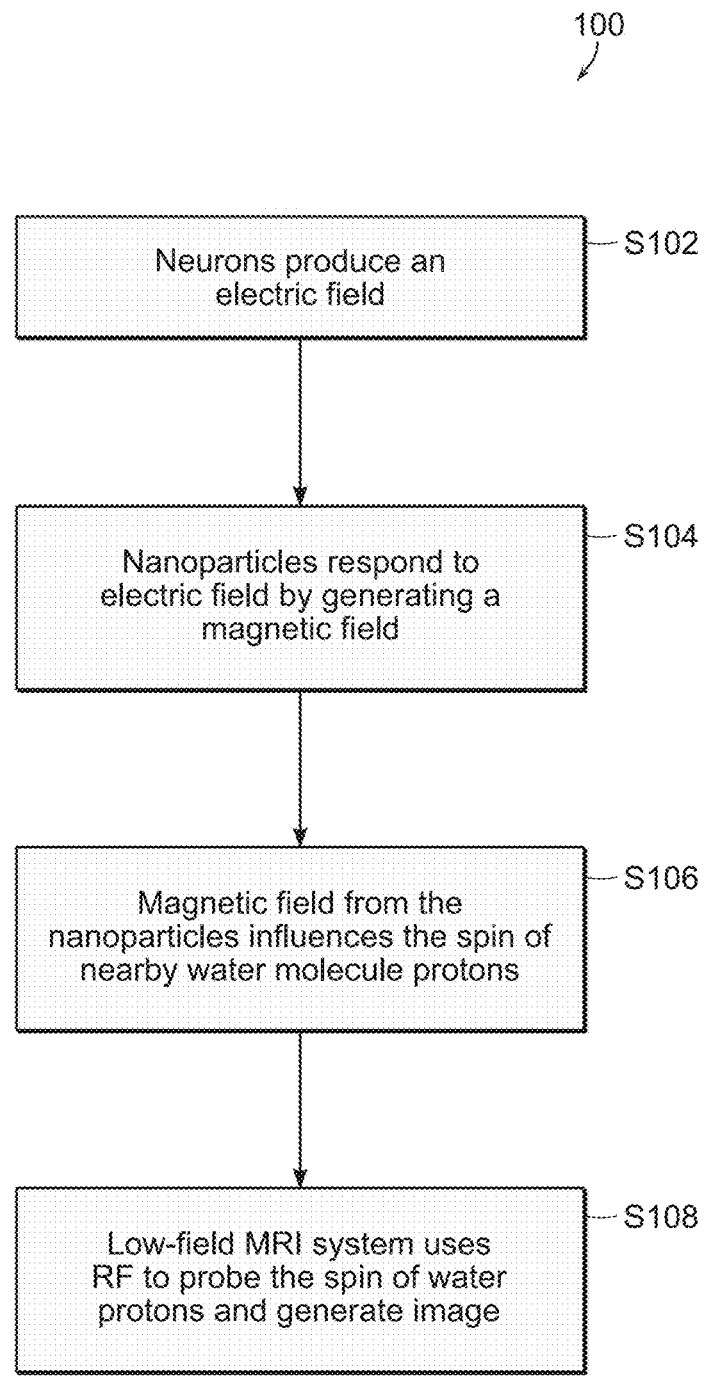
FIG. 4 includes a logical flow diagram of the logical flow of a method for imaging neuronal currents in a human brain using nanoparticles and low-field magnetic resonance imaging (MRI), according to some exemplary embodiments.

FIGS. 3A through 3D include schematic diagrams illustrating an approach to imaging neuronal currents in a human brain using nanoparticles and low-field magnetic resonance imaging (MRI), according to some exemplary embodiments. FIG. 4 includes a logical flow diagram of the logical flow of a method 100 for imaging neuronal currents in a human brain using nanoparticles and low-field magnetic resonance imaging (MRI), according to some exemplary embodiments. Referring to FIGS. 3A through 3D and 4, as illustrated in FIG. 3A, neurons in brain 13 produce an electric field, in step S102. As illustrated in FIG. 3B, nanoparticles 12 respond to this electric field E by generating and/or altering a local magnetic field B, in step S104. As illustrated in FIG. 3C, the magnetic field B from the nanoparticles influences the spin of nearby water molecule protons 22, in step S106. As illustrated in FIG. 3D, low-field MRI system 16 uses RF to probe the spin of water protons 22 and generate image 18.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A method of imaging in connection with electrical currents, comprising:
   introducing nanoparticles into a region in which the electrical currents are present; and
   detecting an effect of a magnetic field generated by interaction of the nanoparticles with the electrical currents in the region, using a low-field magnetic resonance imaging (MRI) scanner, the MRI scanner operating at a magnetic field intensity below a level at which the nanoparticles would be magnetically saturated.

2. The method of claim 1, wherein the electrical currents are neuronal currents.

3. The method of claim 1, wherein the region comprises at least a portion of a human brain.

4. The method of claim 1, wherein the magnetic field intensity is below 0.1 Tesla.

5. The method of claim 1, wherein the nanoparticles comprise a ferromagnetic material.

6. The method of claim 5, wherein the nanoparticles comprise a ferroelectric material.

7. The method of claim 1, wherein the nanoparticles comprise a ferroelectric material.

8. The method of claim 1, wherein the nanoparticles comprise cobalt ferrite.

9. The method of claim 8, wherein the nanoparticles comprise barium titanate.

10. The method of claim 1, wherein the nanoparticles comprise barium titanate.

11. A system for imaging in connection with electrical currents, comprising:
    nanoparticles in a region in which the electrical currents are present; and
    a low-field magnetic resonance imaging (MRI) scanner for detecting an effect of a magnetic field generated by interaction of the nanoparticles with the electrical currents in the region, the MRI scanner operating at a magnetic field intensity below a level at which the nanoparticles would be magnetically saturated.

12. The system of claim 11, wherein the electrical currents are neuronal currents.

13. The system of claim 11, wherein the region comprises at least a portion of a human brain.

14. The system of claim 11, wherein the magnetic field intensity is below 0.1 Tesla.

15. The system of claim 11, wherein the nanoparticles comprise a ferromagnetic material.

16. The system of claim 15, wherein the nanoparticles comprise a ferroelectric material.

17. The system of claim 11, wherein the nanoparticles comprise a ferroelectric material.

18. The system of claim 11, wherein the nanoparticles comprise cobalt ferrite.

19. The system of claim 18, wherein the nanoparticles comprise barium titanate.

20. The system of claim 11, wherein the nanoparticles comprise barium titanate.

* * * * *